(12) United States Patent
Ahn et al.

(10) Patent No.: US 8,645,078 B2
(45) Date of Patent: Feb. 4, 2014

(54) METHOD AND APPARATUS FOR RECOVERING GENE SEQUENCE USING PROBE MAP

(75) Inventors: Tae-jin Ahn, Seoul (KR); Soyeon Ahn, Seoul (KR); Sung-ho Won, Seoul (KR); Su-hyeon Kim, Seoul (KR); Taesung Park, Seoul (KR); Sung-young Lee, Seoul (KR); Seung-yeoun Lee, Seoul (KR); Bora Yeon, Seoul (KR); Young-ho Park, Bucheon-si (KR)

(73) Assignees: Samsung Electronics Co., Ltd., Suwon-Si, Gyeonggi-Do (KR); SNU R&DB Foundation, Seoul (KR)

( * ) Notice: Subject to any disclaimer, the term of this patent is extended or adjusted under 35 U.S.C. 154(b) by 75 days.

(21) Appl. No.: 13/303,861

(22) Filed: Nov. 23, 2011

(65) Prior Publication Data

US 2012/0173157 A1    Jul. 5, 2012

(30) Foreign Application Priority Data

Jan. 4, 2011    (KR) ........................ 10-2011-0000548

(51) Int. Cl.
- *G06F 19/00* (2011.01)
- *G11C 17/00* (2006.01)
- *G06F 15/00* (2006.01)

(52) U.S. Cl.
USPC .................................. 702/20; 365/94; 700/1

(58) Field of Classification Search
None
See application file for complete search history.

(56) References Cited

U.S. PATENT DOCUMENTS

2008/0228457 A1   9/2008   Mishra et al.
2009/0099786 A1   4/2009   Oliver et al.

OTHER PUBLICATIONS

Altman et al. The normal distribution British Medical Journal vol. 310, p. 298 (1995).*
Johnson an extended IUPAC nomenclature code for polymorphic nucleic acids Bioinformatics vol. 26, pp. 1386-1389 (2010).*
Huang, J. et al., A comparison of physical mapping algorithms based on the maximum likelihood model, Bioinformatics, 2003, 19(11):1303-1310.
Drmanac, R. et al., Sequencing by Hybridization (SBH): Advantages, Achievements, and Opportunities, Adv Biochem Eng Biotechnol. 2002, 77: 75-101.
Heber, S. et al.,Contig Selection in Physical Mapping, J. Comp. Biol. 2000, 7(3/4): 395-408.
Labat, I. and Drmanac, R., Simulations of ordering and sequence reconstruction of random DNA clones hybridized with a small number of oligomeric probes. Report of work sponsored by an Agency of the United States government. 1992. 27 pages.

* cited by examiner

*Primary Examiner* — John S Brusca
(74) *Attorney, Agent, or Firm* — Leydig, Voit & Mayer, Ltd.

(57) ABSTRACT

A method of recovering a nucleic acid sequence using a probe map includes: aligning a probe onto a target sequence based on a result in which the probe is hybridized to the target sequence; determining a representative value representing each aligned position of the probe; and recovering a base sequence of the target sequence by using a probe map to which the determined representative values and base sequence information of the probe are mapped.

18 Claims, 14 Drawing Sheets

FIG. 4

| <PROBE> | <DETECTED POSITION> |
|---|---|
| gcgcct 5 | 9645, 10154, 10571, 19406, 20107 |
| gcgcct 5 | 9640, 10157, 10563, 19451, 20117 |
| gcgcct 5 | 9635, 10162, 10551, 19416, 20131   401 |
| gcgcct 5 | 9614, 10147, 10575, 15000, 19423, 20122 |
| gcgcct 5 | 9645, 10127, 10543, 19432, 20105 |
| gcgcct 5 | 9653, 10152, 10564, 19455, 20194 |
| gcgcct 5 | 9646, 10147, 10554, 19451, 20113 |
| gcgcct 5 | 9674, 10163, 10543, 19444, 20102 |
| gcgcct 8 | 1000, 9675, 10156, 10531, 19452, 20107, 50000, 50500 |
| gcgcct 7 | 1000, 9641, 10155, 10543, 19476, 20135, 50000 |
| gcgcct 7 | 1000, 9642, 10151, 10563, 19458, 20104, 50000 |
| gcgcct 5 | 9645, 10156, 10574, 19472, 20103 |
| gcgcct 5 | 9643, 10158, 10573, 19434, 20121 |
| gcgcct 5 | 9625, 10156, 10572, 19455, 20139   402 |
| gcgcct 5 | 9645, 10164, 10570,     , 20103  19447 |
| gcgcct 5 | 9615, 10175, 10569, 19458, 20102 |
| gcgcct 5 | 9655, 10171, 10571, 19461, 20115 |
| gcgcct 5 | 9645, 10153, 10575, 19453, 20134 |
| gcgcct 5 | 9642, 10138, 10573, 19485, 20146 |
| gcgcct 5 | 9645, 10136, 10559, 19454, 20157 |
| gcgcct 5 | 9625, 10154, 10583, 19452, 20108 |
| gcgcct 5 | 9615, 10164, 10554, 19458, 20199 |
| gcgcct 5 | 9643, 10183, 10564, 19450, 20120 |
| gcgcct 5 | 9641, 10186, 10574, 19453, 20134 |
| gcgcct 5 | 9611, 10117, 10543, 19453, 20104 |
| gcgcct 5 | 9626, 10135, 10532, 19453, 20122 |
| gcgcct 5 | 9637, 10172, 10564, 19455, 20115 |
| gcgcct 5 | 9641, 10153, 10575, 19452, 20136 |
| gcgcct 5 | 9643, 10113, 10576, 19453, 20113 |
| gcgcct 5 | 9640, 10132, 10586, 19459, 20192 |

| size error (sigma) | replicate | recovered seq (%) |
|---|---|---|
| 0 | 1 | 100 |
| 10 | 1 | 92.78 |
| 10 | 10 | 94.32 |
| 10 | 30 | 95.79 |
| 50 | 1 | 71.06 |
| 50 | 10 | 73.18 |
| 50 | 30 | 75.58 |
| 100 | 1 | 52.53 |
| 100 | 10 | 55.08 |
| 100 | 30 | 56.85 |

METHOD AND APPARATUS FOR RECOVERING GENE SEQUENCE USING PROBE MAP

CROSS-REFERENCE TO RELATED APPLICATIONS

This application claims the benefit of Korean Patent Application No. 10-2011-0000548, filed on Jan. 4, 2011, in the Korean Intellectual Property Office, the disclosure of which is incorporated herein in its entirety by reference.

BACKGROUND

1. Field

The present disclosure relates to a method and apparatus for recovering a nucleic acid sequence by using data of a probe map generated with a plurality of probes.

2. Description of the Related Art

According to the development of technology in the biotechnology field, deoxyribonucleic acid (DNA) sequences consisting of genetic information of individuals have been used in various fields, such as trait transformation and disease tracing, since a DNA sequence was identified. Analysis of a DNA sequence, i.e., DNA sequencing, is widely utilized to search for a gene involved in development of a disease, such as diabetes or cancer, or to determine a relationship between genetic diversity and a developmental characteristic of an individual. In particular, gene information collected from individuals is important to investigate and reveal genetic characteristics associated with different symptoms or progression of a disease. Thus, DNA sequence information of individuals is core data to prevent diseases by perceiving current and future disease-related information or to select an optimal treatment in an initial stage of a disease. Accordingly, to be used as a medical tool for individuals, DNA sequencing technology capable of correctly perceiving individual DNA sequence information is required.

SUMMARY

Provided are a method and apparatus for recovering a nucleic acid sequence by using data of a probe map generated with a plurality of probes.

Provided is a computer-readable recording medium storing a computer-readable program for executing the method.

Additional aspects of the invention will be set forth in part in the description which follows and, in part, will be apparent from the description, or may be learned by practice of the presented exemplary embodiments.

According to an aspect of the invention, there is provided a method of recovering a nucleic acid sequence using a probe map, the method including: aligning a probe having a base sequence of a predetermined length onto a target sequence based on a result in which the probe is hybridized in the target sequence; determining a representative value representing each aligned position of the probe based on a statistical distribution of the aligned positions of the probe; and recovering a base sequence of the target sequence by using a probe map to which the determined representative values and base sequence information of the probe are mapped, wherein the alignment and the determination are repeatedly performed for other probes having base sequences different from the probe, and the probe map contains mapping information of the used probes.

According to another aspect of the present invention, there is provided a computer-readable recording medium storing a computer-readable program for executing the method of recovering a nucleic acid sequence.

According to another aspect of the present invention, there is provided an apparatus for recovering a nucleic acid sequence using a probe map, the apparatus including: a probe alignment unit which aligns a probe having a base sequence of a predetermined length into a target sequence based on a result in which the probe is hybridized in the target sequence; a representative value determiner which determines a representative value representing each of aligned positions of the probe based on a statistical distribution on the aligned positions of the probe; and a recovering unit which recovers a base sequence of the target sequence by using a probe map to which the determined representative values and base sequence information of the probe are mapped, wherein the probe alignment unit and the representative value determiner repeatedly perform the alignment and the determination for other probes having base sequences different from the probe, respectively, and the probe map contains mapping information of the used probes.

BRIEF DESCRIPTION OF THE DRAWINGS

These and/or other aspects will become apparent and more readily appreciated from the following description of the exemplary embodiments, taken in conjunction with the accompanying drawings of which:

FIG. 4 shows positions of a repeatedly detected probe according to an embodiment of the invention;

DETAILED DESCRIPTION

Figure 1A:
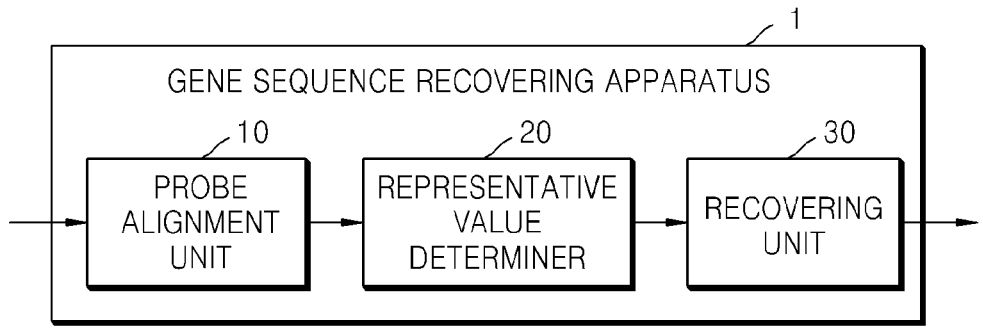
FIG. 1A is a block diagram of a nucleic acid sequence recovering apparatus according to an embodiment of the invention.

Reference will now be made in detail to exemplary embodiments, examples of which are illustrated in the accompanying drawings, wherein like reference numerals refer to like elements throughout. In this regard, embodiments of the invention may have different forms and should not be construed as being limited to the descriptions set forth herein. Accordingly, the exemplary embodiments are merely described below, by referring to the figures, to explain aspects of the invention.

FIG. 1A is a block diagram of a nucleic acid sequence recovering apparatus 1 according to an embodiment of the invention. Referring to FIG. 1A, the nucleic acid sequence recovering apparatus 1 includes a probe alignment unit 10, a representative determiner 20, and a recovering unit 30. Only components related to the current embodiment are shown in the nucleic acid sequence recovering apparatus 1 of FIG. 1A. Thus, it will be understood by those of ordinary skill in the art that other general-purpose components may be further included in the nucleic acid sequence recovering apparatus 1.

The probe alignment unit 10, the representative determiner 20, and the recovering unit 30 of the nucleic acid sequence recovering apparatus 1 shown in FIG. 1A may correspond to one or a plurality of processors. Each of the processors may be implemented with an array of a plurality of logic gates or a combination of a general-purpose microprocessor and a memory for storing programs executable in the microprocessor. In addition, it will be understood by those of ordinary skill in the art that the processor may be implemented with hardware in another form.

The nucleic acid sequence recovering apparatus 1 according to the current embodiment is a device capable of analyzing deoxyribonucleic acid (DNA) sequence information of individuals. A variety of biometric information is represented with genes of DNA sequences. Thus, full DNA sequence information of an individual is useful to understand a life phenomenon and obtain disease-related information. For example, DNA sequence information of an individual contains disease-related information from the past to the future. Thus, if DNA sequence information of an individual can be correctly perceived, diseases may be prevented, or an optimal treatment may be selected for an initial stage or a subsequent state of a disease.

Analysis of DNA sequence information, i.e., DNA sequencing, means determination of the DNA sequence in a target sequence.

One commonly used DNA sequencing method is Sequencing-By-Hybridization (SBH). The basic concept of SBH maybe described schematically in two stages. The first stage is detecting sets of base sequences within a target sequence by using sequence-specific probes to hybridize to the target sequence. The second stage is constructing the complete, linearly ordered target sequence by combining and overlapping the detected base sequences.

However, conventional DNA sequencing methods, including SBH, have problems. In more detail, a probe having a base sequence complementary to a predetermined base sequence of a target sequence may not hybridize, or bind, to the correct position, i.e. to complementary base sequence, of the target sequence, i.e., a phenomenon in which the probe is hybridized in a totally different position of the target sequence or is not hybridized at all to the target sequence may occur. Thus, conventional DNA sequencing methods may not perform accurate DNA sequencing due to such problems. In addition, since conventional DNA sequencing methods recover a target sequence by considering only a one directional base sequence order or recover a target sequence without generating branches for each case when the number of cases of a base in a position to be recovered is plural, accurate and efficient DNA sequencing may not be performed.

That is, when a perfectly complementary hybridization between a target sequence and probes is not performed, i.e., when an imperfect hybridization with at least one unmatched position is performed, the target sequence recovered in a conventional DNA sequencing method has a base sequence different from the original target sequence.

However, when a probe is hybridized with the target sequence within a predetermined range of mismatch with a portion of the target sequence having the complementary base sequence of the target sequence, the nucleic acid sequence recovering apparatus 1 according to the invention more accurately recovers the target sequence by considering both the case where the probe is hybridized in a position totally different from the portion and the case where the probe is not hybridized in the portion. In addition, since the nucleic acid sequence recovering apparatus 1 according to the current embodiment considers base sequence order in both directions, i.e., the 5' to 3' direction and the 3' to 5' direction, when the target sequence is recovered, the nucleic acid sequence recovering apparatus 1 according to the current embodiment may more efficiently recover the target sequence.

Furthermore, when the number of cases of a base in a position to be recovered is plural, for example at a polymorphic site, the nucleic acid sequence recovering apparatus 1 according to the current embodiment may recover a target sequence closer to the original base sequence by generating several target sequence candidates as branches corresponding to the possible cases and recovering the most proper one among the target sequence candidates as the target sequence.

Hereinafter, the detailed function and operation of a nucleic acid sequence recovering apparatus 1 according to the current embodiment is described in more detail.

The probe alignment unit 10 aligns a probe onto a target sequence based on the result in which the probe having a base sequence of a predetermined length is hybridized with the target sequence. Although the current embodiment is described below with the predetermined length of the probe assumed to be a 6-mer, this is merely for simplification of the description of the current embodiment, and the predetermined length of a probe in the current embodiment is not limited thereto.

The probe alignment unit 10 receives a result in which a first kind of probe, among various kinds of probes having different base sequences, is hybridized to a target sequence. The probe alignment unit 10 sequentially receives the results in which the other kinds of probes having different base sequences are hybridized to the target sequence after completing alignment of the first kind of probe and aligns the other kinds of probes.

Figure 1B:
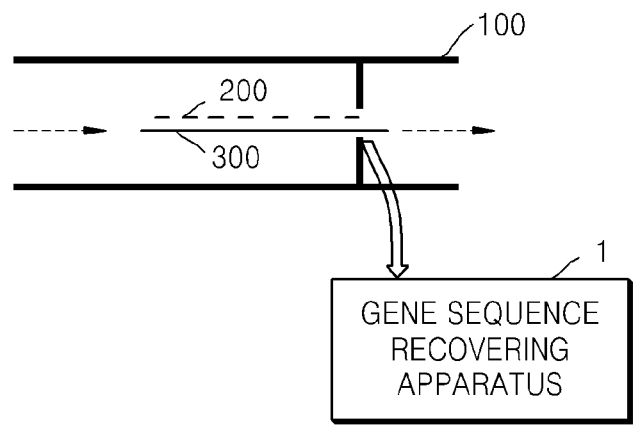
FIG. 1B is a diagram of the nucleic acid sequence recovering apparatus connected to a nanopore device, according to an embodiment of the invention.

FIG. 1B is a diagram of the nucleic acid sequence recovering apparatus 1 connected to a nanopore device 100, according to an embodiment of the present invention. Referring to FIG. 1B, the nucleic acid sequence recovering apparatus 1 is connected to the nanopore device 100 capable of detecting the position of a probe 200 hybridized to a target sequence 300 and receives the detected position results from the nanopore device 100. Although a generally known nanopore may be used as a device for detecting the result in which probe 200 is hybridized to target sequence 300, the current embodiment is not limited to use of any one detection device; the only requirement for the detection device is that it can detect the result in which the probe 200 is hybridized to single-stranded DNA.

Referring back to FIG. 1A, the base sequence of a probe to be aligned with a target sequence is predefined. However, the target sequence to be recovered has an unknown base sequence. A 6-mer probe is hybridized to a position of the target sequence having a 6-mer base sequence complementary to the 6-mer probe. The target sequence may have one or more positions of sequence complementarity with the probe, and in this case, the probe may be hybridized to all of the positions of complementary sequence in the target sequence.

The probe alignment unit 10 aligns a probe so that the error of the position in which the probe is hybridized is minimized. As described above, when a probe is hybridized to a target sequence, the probe may be hybridized to a correct position of the target sequence. However, the probe may be hybridized to a mismatched position, or may not be hybridized at all. Thus, the target sequence may be more accurately recovered by aligning the probes to be error-robust with respect to all cases where errors occur.

Figure 2:
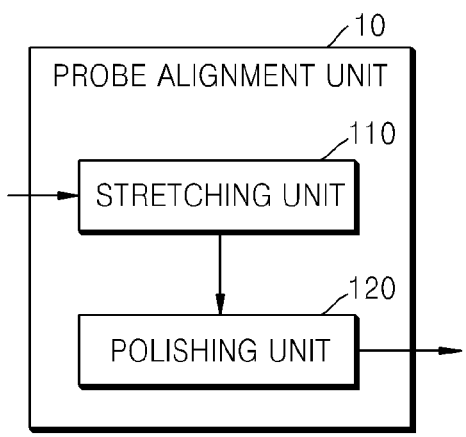
FIG. 2 is a block diagram of a probe alignment unit according to an embodiment of the invention.

FIG. 2 is a block diagram of the probe alignment unit 10 according to an embodiment of the present invention. Referring to FIG. 2, the probe alignment unit 10 includes a stretching unit 110 and a polishing unit 120.

The stretching unit 110 generates a probe map including mapping information of a probe by aligning the probe from repeatedly detected hybridization results with a given target sequence based on errors of positions in which the probe is hybridized.

Figure 3:
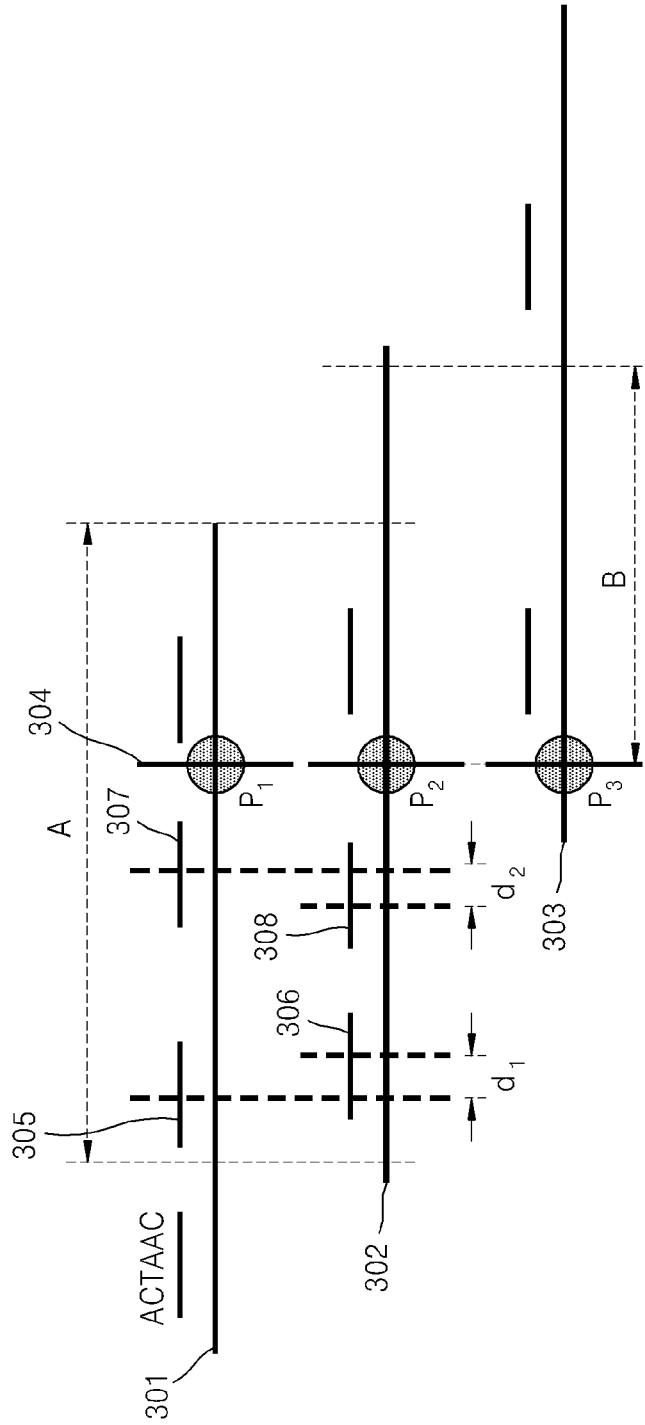
FIG. 3 is a schematic diagram showing alignment of probes performed by a stretching unit according to an embodiment of the invention.

FIG. 3 is a schematic diagram showing alignment of probes performed by the stretching unit 110 according to an embodiment of the invention. Referring to FIG. 3, repeatedly detected results are shown in which probes 305, 306, 307, and 308, all having the same base sequence ACTAAC, are hybridized to the same single-stranded target sequences 301, 302, and 303. Although an example in which the result obtained by detecting a hybridized result three times is shown in FIG. 3, the current embodiment is not limited thereto.

In more detail, the probes 305, 306, 307, and 308 are complementarily bound with a target sequence. The base sequence of the target sequence complementarily bound with the probes 305, 306, 307, and 308 is TGATTG. To compare the hybridized results with each other, a position 304 in which the target sequences 301, 302, and 303 overlap each other is selected. In an ideal case, when the overlapping region of the target sequence 301 in the first row and the target sequence 302 in the second row is region A, the positions in which the probes 305 and 306 or the positions in which the probes 307 and 308 are hybridized are identical, respectively. However, the positions at which the probes 305, 306, 307, and 308, respectively, are detected are a little different. This is because a size error exits in the detected positions at which the probes 305, 306, 307, and 308 are hybridized.

In FIG. 3, the value of $d_i$–$d_j$ means an error of a predetermined level due to a difference between the positions of the probes 305 and 306 ($d_i$) and the difference between the positions of probes 307 and 308 ($d_j$). For example, although it is expected that the probes 305 and 306 are located in the same position in FIG. 3, a difference between the detected positions occurs due to experimental errors of various causes, e.g., a size error. If it is assumed that the probes 305 and 306 are in the same positions on an actual DNA molecule, when hybridized results are repeatedly measured, it is expected that the average of size errors is 0.

As described above, the stretching unit 110 aligns probes 305, 306, 307, and 308 on the target sequence so that errors of all hybridized positions of probes 305, 306, 307, and 308 are minimized as shown in FIG. 3.

When only size errors exist for detected hybridized positions, the error between the detected hybridized positions in different target sequences 301, 302, and 303 for a given position (i) in the target sequence is defined as $d_i$. For example, an error between hybridized positions of the probes 305 and 306 in a region A of the target sequences 301 and 302 is $d_1$, and an error between hybridized positions of the probes 307 and 308 in the region A of the target sequences 301 and 302 is $d_2$. It may be assumed that $d_1$ and $d_2$ obey a normal distribution $N(0, \sigma^2)$. Likewise, $d_i$ may be obtained in a region B of the target sequences 302 and 303 in the same way, and it may be assumed that $d_i$ obeys a normal distribution $N(0, \sigma^2)$. That is, a likelihood function of $d_i$ is $L(d_1, \ldots, d_k) \propto [\Pi \phi(d_i/\sigma)]$, which can be obtained by calculating $d_i$ from the relative distances of the probes 305, 306, 307, and 308 and using $d_i \sim N(0, \sigma^2)$, where $\phi$ denotes a probability distribution function of a standard normal distribution.

The stretching unit 110 aligns the probes 305, 306, 307, and 308 by applying a Metropolis-Hastings algorithm to the probe position-related likelihood function so that the hybridized positions of the probes 305, 306, 307, and 308 are most properly reflected. Since it is well known to those of ordinary skill in the art that the Metropolis-Hastings algorithm is applied to a likelihood function, a detailed description thereof is omitted.

This process may be performed as an algorithm disclosed in Table 1.

TABLE 1

In an $n^{th}$ operation,
1. $P_1, \ldots, P_{30}$ are updated: $P_i^* \leftarrow P_i^{n-1} + N(0, 1^2)$, i=1, ..., 30.
    $P_i^{n-1}$ denotes an $i^{th}$ replicate position calculated in an $(n-1)^{th}$ operation, wherein "replicate" means a DNA sequence with probe mapped position.
2. $d_i$ is calculated using ($P_1, \ldots, P_{30}$).
3. A likelihood $L^*$ of $d_i$ is calculated: the likelihood is a distribution function of size errors.
4. After randomly generating a in $U(0, 1)$, if $a < L^*/L_{n-1}$,
    $x_1^n \leftarrow x_1^*; \ldots; x_{30}^n \leftarrow x_1^*$,
where $X_i$ is a position of the $i^{th}$ replicate which satisfies maximum likelihood condition, and
    if $a > L^*/L_{n-1}$,
    $x_1^n \leftarrow x_1^{n-1}; \ldots; x_{30}^n \leftarrow x_{30}^{n-1}$.

FIG. 4 shows a table showing detected positions of a probe repeatedly hybridized to a target sequence according to an embodiment of the present invention. Referring to FIG. 4, each of the lines shows the detected positions of a base sequence GCGCCT of a probe to a target sequence determined during one of the 30 repeated hybridization detection times. Here, the positions at which the probe is hybridized vary a little at every repeated detection time. In addition, FIG. 4 also shows a case 401 in which the probe is hybridized in a totally different position and a case 402 in which the probe is not hybridized at a position present in the other detection times. As described above, the stretching unit 110 aligns the probe based on the data of repeatedly detected positions of the probe as shown in FIG. 4.

Referring back to FIG. 2, the stretching unit 110 generates a probe map, which is a mapping table into which the base sequence information of a used probe and the aligned positions of the probe are mapped.

The polishing unit 120 refines the mapping information of the currently aligned probe by using the mapping information of other probes contained in the probe map. The polishing unit 120 performs alignment by referring to mapping information contained in the probe map for probes having a base sequence in which at least one base is different from the base sequence of the currently aligned probe f.

In the probe map, information regarding base sequences of various kinds of probes and information regarding positions in which a corresponding probe is hybridized in a target sequence are mapped. That is, the probe map includes all of mapping information regarding previously aligned probes and is continuously updated with mapping information regarding a currently used probe.

A refining process of the polishing unit 120 will now be described in more detail.

For example, when the polishing unit 120 refines the mapping information of the currently aligned probe ACTAAC, the polishing unit 120 refines the mapping information of the probe ACTAAC by using the mapping information in the probe map of 4 different 6-mer probes CTAACA, CTAACC, CTAACG, and CTAACT starting from the sequence CTAAC remaining after excluding the first base of the probe ACTAAC and the mapping information in the probe map of 4 different 6-mer probes AACTAA, CACTAA, GACTAA, and TACTAA ending with the sequence ACTAA, remaining after excluding the last base from the probe ACTAAC. These different probes have a one-base difference from the currently aligned probe ACTAAC.

That is, the polishing unit 120 uses the mapping information of the additional 8 different 6-mer probes to refine the mapping information of the probe ACTAAC. The mapping information of the different probes is used because probes located before and after 1 bp of the probe ACTAAC necessarily belong to the 8 probes. The polishing unit 120 refines mapping information of a currently aligned probe by using this feature described above.

Figure 5:
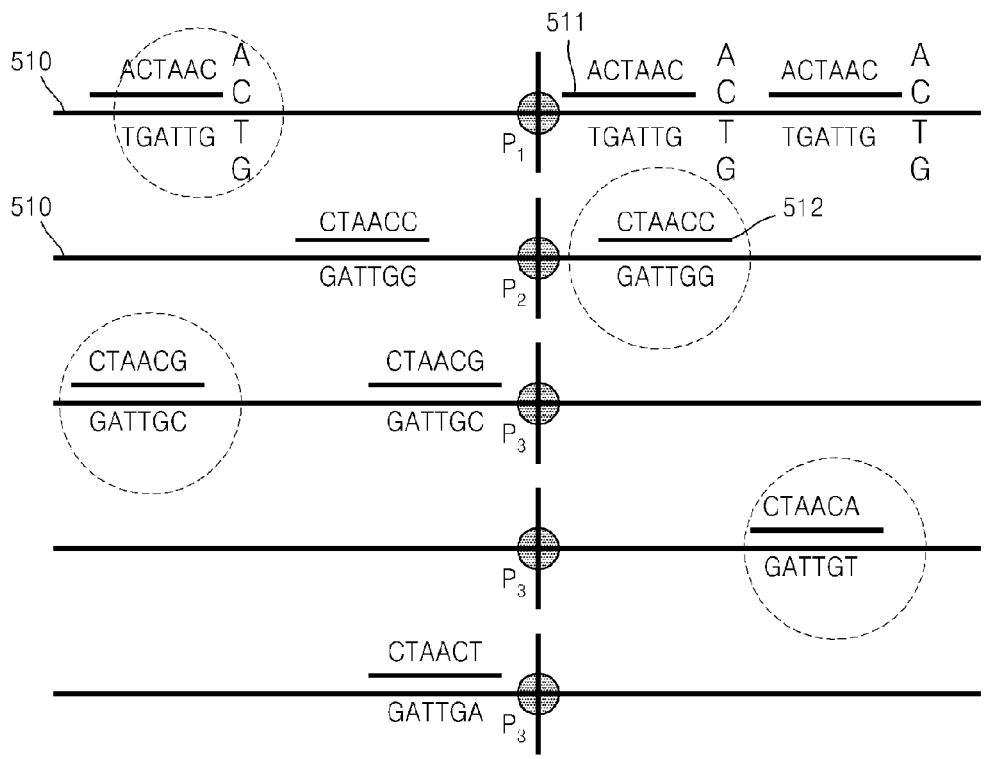
FIG. 5 is a schematic diagram showing a process performed by a polishing unit to refine aligned positions of probes, according to an embodiment of the invention.

FIG. 5 shows a process performed by the polishing unit 120 to refine aligned positions of probes, according to an embodiment of the invention. Referring to FIG. 5, positions in which different probes are hybridized in a target sequence 510 are shown. Mapping information to which information regarding base sequences of probes and information regarding hybridized positions of the probes are mapped is stored in a probe map.

Referring to FIG. 5, the polishing unit 120 aligns a probe 511 to be currently refined by referring to mapping information of a probe having a base sequence in which at least one base is different from the probe 511. For example, the probe 511 ACTAAC has a base sequence in which a base is different from probe 512 CTAACC, and the probe 511 and the probe 512 are hybridized in similar positions of the target sequence 510. Thus, when both the base sequence TGATTG of the target sequence 510 to which the probe 511 is hybridized and the base sequence GATTGG of the target sequence 510 to which the probe 512 is hybridized are considered, the probes 511 and 512 are aligned in correct positions. If the other positions of the probe ACTAAC are not correctly aligned, the polishing unit 120 refines the positions by referring to mapping information of the other probes so that the other positions are aligned in correct positions. Accordingly, the polishing unit 120 refines aligned positions of all of the probes.

Referring back to FIG. 1A, after completing alignment of probes in the probe alignment unit 10, a process of determining a representative value in the representative value determiner 20 is described.

The representative value determiner 20 determines a representative value representing each of the aligned positions of a probe based on the statistical distribution of each of the aligned positions. If the statistical distribution is a normal distribution, the representative value determiner 20 determines a value representing the normal distribution as the representative value.

Figure 6:
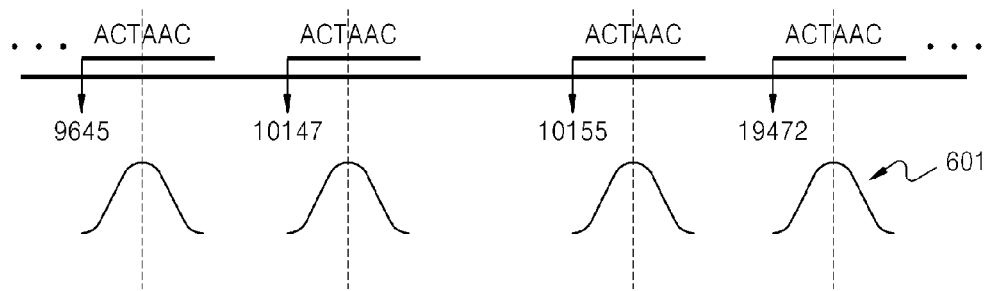
FIG. 6 is a schematic diagram showing a process performed by a representative value determiner to determine representative values of positions of a probe, according to an embodiment of the invention.

FIG. 6 shows a process performed by the representative value determiner 20 to determine representative values of positions of a probe, according to an embodiment of the invention. Referring to FIG. 6, a statistical distribution 601 of each of aligned position of a probe in a target sequence is shown. The representative value determiner 20 determines a value representing the position of the probe from the statistical distribution 601 of a given position at which the probe is aligned. The representative value is a value representing the position at which the probe is hybridized in a target sequence.

When the statistical distribution 601 shown in FIG. 6 is a normal distribution, the representative value determiner 20 determines a value representing the normal distribution as the representative value. For example, the representative value determiner 20 determines a value corresponding to the mean value of the normal distribution as the representative value, and it is determined that the position of the probe is the position corresponding to the representative value in the target sequence.

However, if each statistical distribution is not a normal distribution, the representative value determiner 20 uses a resampling algorithm and the Metropolis-Hastings algorithm by performing a repetitive simulation (e.g., Monte Carlo simulation) with a mathematical model of a Markov chain for a likelihood function based on the statistical distribution. Since it is well known to those of ordinary skill in the art that the resampling and Metropolis-Hastings algorithms are applied to a likelihood function through Markov Chain Monte Carlo (MCMC) simulations, a detailed description thereof is omitted.

As a result, the representative value determiner 20 determines a representative value representing each of the aligned positions of a probe in a target sequence, and it is determined that each position of the probe in the target sequence is the position corresponding to the representative value in the target sequence.

As a result, the representative value determiner 20 determines through the above-described process that the probe of FIG. 6 hybridizes to the target sequence at positions 9645, 10147, 10155, and 19472 in the target sequence.

Referring back to FIG. 1A, the probe alignment unit 10 and the representative value determiner 20 repeatedly perform the above-described process for the other probes having different base sequences. That is, after aligning any one probe and determining representative values for the probe, the probe alignment unit 10 and the representative value determiner 20 align the other probes and determine representative values for the other probes in the same way as described above. The probe map stores the mapping information of the probes used in the process.

As described above, when 6-mer probes are used in the current embodiment, the probe alignment unit 10 and the representative value determiner 20 perform the above-described process for a set of 6-mer probes having all possible 6-mer base sequences ($4^6$). That is, the probe alignment unit 10 and the representative value determiner 20 perform the above-described process for all probes of AAAAAA, AAAAAT, AAAAAG, AAAAAC, ... (omitted), CCGCGA, CCGCGT, CCGCGG, CCGCGC, ..., (omitted), CCCCCC. However, it will be understood by those of ordinary skill in the art that a user may selectively use only a portion of sets of base sequences of the probes according to a using environment.

After acquiring mapping information of probes to be included in the probe map by the probe alignment unit 10 and the representative value determiner 20, the recovering unit 30 recovers a base sequence of the target sequence.

The recovering unit 30 recovers the base sequence of the target sequence by using the probe map to which the determined representative values and the base sequence information of the probes are mapped.

In more detail, the recovering unit 30 recovers the target sequence at a position to be recovered by using information regarding the base sequences of the probes aligned at positions neighboring the position to be recovered in the target sequence, included in the probe map. In this case, the recovering unit 30 recovers the target sequence by using information regarding the positions and the base sequences of probes aligned at positions neighboring the position to be recovered in both the 5' end direction and the 3' end direction. Here, the recovery in the 5' end direction is recovering the target sequence in a prefix direction of the base sequence, and the recovery in the 3' end direction is recovering the target sequence in a suffix direction of the base sequence.

The recovering unit 30 recovers the target sequence by dividing a range to be recovered into, for example, 500 bp. However, the range to be recovered is not limited to 500 bp. The recovering unit 30 selects a position to be initially recovered. Thereafter, the recovering unit 30 recovers the target sequence in a unit identical to a probe length, e.g., a 6-bp unit.

At this time, an error that the recovering unit 30 cannot determine which base is recovered in a position to be recovered in the recovery may occur. That is, the number of cases of a base to be recovered in a position to be recovered may be plural. In this case, the recovering unit 30 generates a plurality of base sequence candidates by generating branches corresponding to the plural number of cases through comparison of values corresponding to errors and a preset threshold. Thereafter, the recovering unit 30 selects the most proper candidate and recovers the selected candidate as a target sequence. This case will be described in more detail with reference to FIGS. 8 and 9A to 9C later.

When all of target sequences included in the recovering ranges (e.g., 500 bp) are recovered, the recovering unit 30 recovers a final target sequence by concatenating the target sequences included in the recovering ranges.

Figure 7:
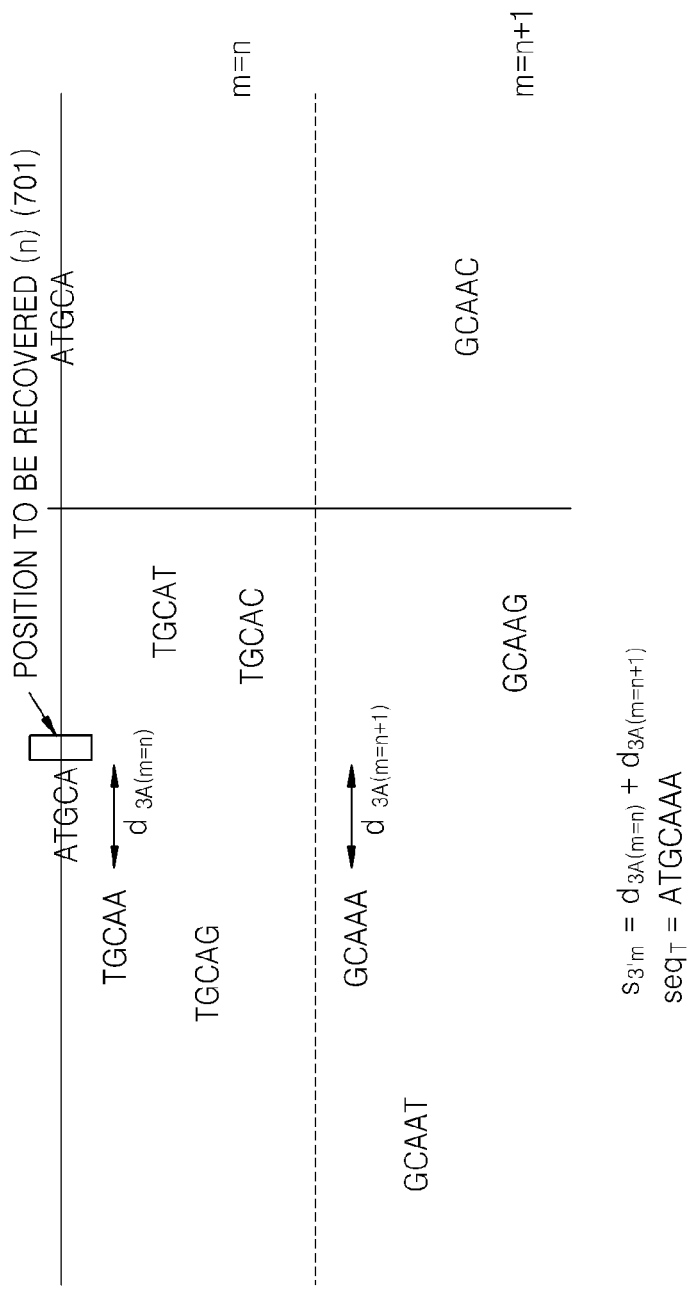
FIG. 7 is a schematic diagram showing a process of recovering a target sequence in a suffix direction, according to an embodiment of the present invention.

FIG. 7 shows a process of recovering a target sequence in the suffix direction, according to an embodiment of the invention. Referring to FIG. 7, a base A, G, T, or C is located at a position (n) 701 to be recovered next to the base sequence ATGCA of the target sequence. The recovering unit 30 uses the probe map to determine which base is used to recover the target sequence in the position 701.

In more detail, the recovering unit 30 refers to mapping information of probes including the base sequence TGCA, which is a portion of the sequence in the suffix direction of the base sequence ATGCA adjacent to position 701 to be recovered in the target sequence, i.e., probes TGCAA, TGCAT, TGCAG, and TGCAC. The recovering unit 30 recovers a base sequence in position 701 by using a probe aligned on the target sequence closest to the base sequence ATGCA from among the probes TGCAA, TGCAT, TGCAG, and TGCAC. That is, since the hybridization position on the target sequence of a probe having the base sequence TGCAA is closest to the position of the base sequence ATGCA, defined as $d_{3A}$ (m=n) in FIG. 7, the base A is recovered in the position 701 to be recovered. The 'd3A' stands for a sequence which ends with a base 'A' at the 3' end (See Table 2). The recovering unit 30 continuously recovers a base of a next position in the suffix direction in the same way as described above. For example, since a position of a probe having a base sequence GCAAA is closest to the base sequence ATGCAA as $d_{3A}$ (m=n+1) in the next position, a base A is recovered in the position 701 to be recovered. As a result recovered two times for example, since a base sequence AA is recovered from the position 701 to be recovered, the original base sequence ATGCA is recovered to ATGCAAA. In FIG. 7, a designation of "m=n" means a step of recovering a sequence at position n, e.g., ATGCA"(?)", where "?" represents the unknown base to be determined at position n and a designation of "m=n+1" means the next step of recovering a sequence at position (n+1) ATGCAA"(?)" after recovering the sequence ATGCA"(A)" at position n. In the case of "m=n", the unknown base "(?)" corresponds to one of the bases A, G, T and C. This base is recovered based on a determination of a certain error ($d_1$) having minimum value among errors ($d_1$) regarding each of sequences TGCAA, TGCAG, TGCAT and TGCAC. Therefore, since the error ($d_1$) of sequence TGCAA is smallest in FIG. 7, the base "(?)" is a base "A". That is, the sequence having the smallest value of the sum (S) of the errors " . . . $d_1(m=n)+d_1(m=n+1)$ . . . " may be recovered. In FIG. 7, "$seq_T$" means a recovered sequence T.

The recovering unit 30 recovers the target sequence in the prefix and suffix directions in the same way as described above. That is, the recovering unit 30 continuously recovers the target sequence by using the closest probe among probes having a base of the position 701 to be recovered until the target sequence is completed. As a result, the final target sequence is recovered so that a sum of $d_{3A}$ (m=n), $d_{3A}$ (m=n+1), and so forth is smallest.

Figure 8:
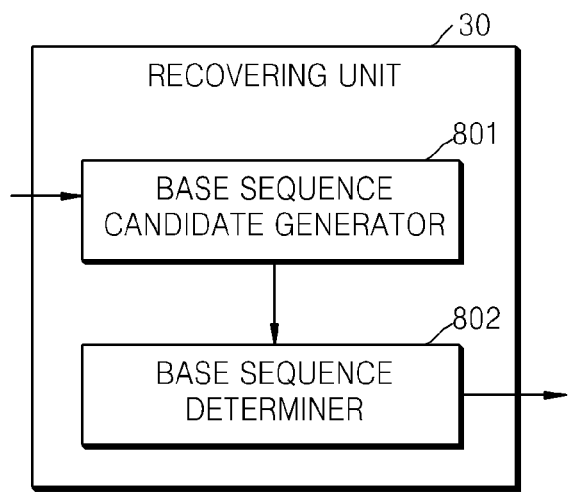
FIG. 8 is a block diagram of a recovering unit according to an embodiment of the invention.

FIG. 8 is a block diagram of the recovering unit 30 according to an embodiment of the invention. Referring to FIG. 8, the recovering unit 30 includes a base sequence candidate generator 801 and a base sequence determiner 802. The recovering unit 30 recovers the base sequence per recovering range as described above.

The base sequence candidate generator 801 generates candidates of base sequences corresponding to a plural number of cases when the number of cases of a base to be recovered is plural in a recovering process. The base sequence determiner 802 determines the most similar base sequence candidate as a base sequence of a target sequence by comparing the generated candidates with a reference sequence.

Figure 9A:
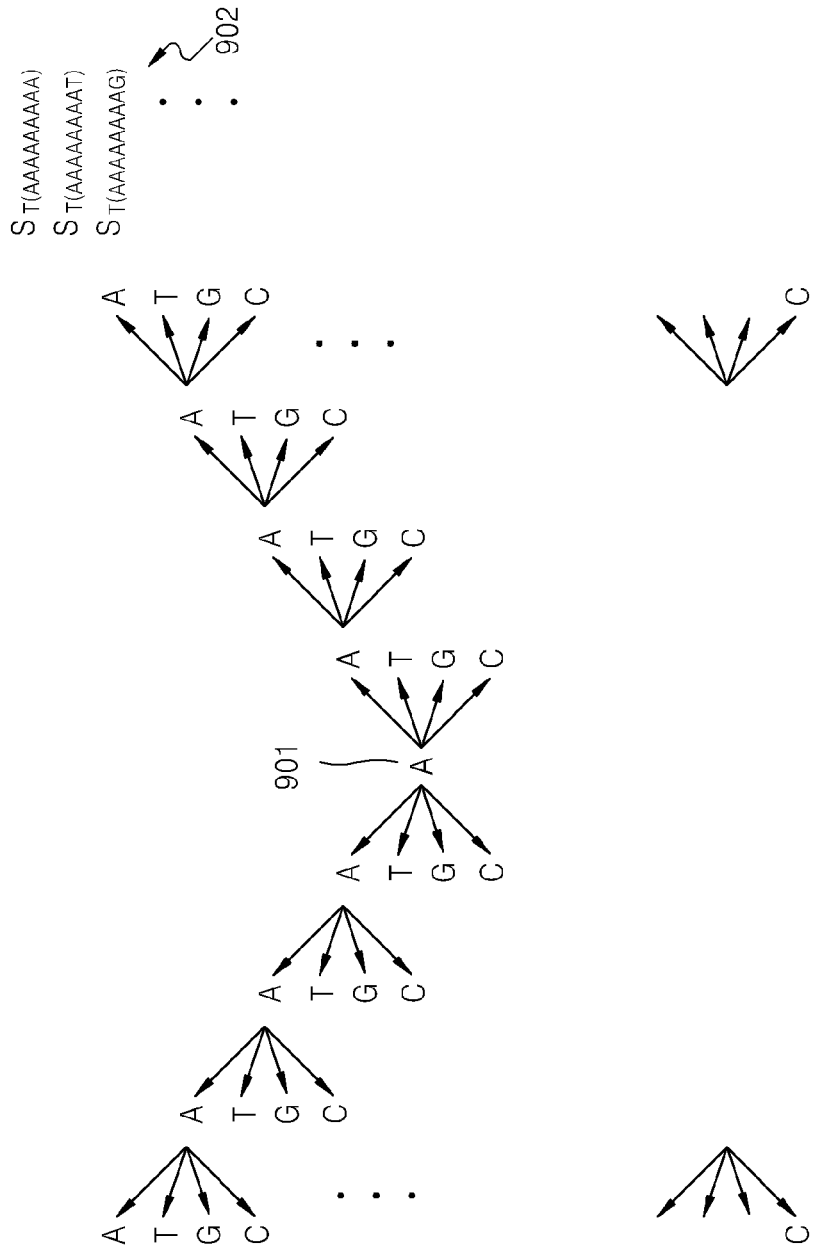
FIG. 9A is a schematic diagram showing branches for generating base sequence candidates in a base sequence candidate generator, according to an embodiment of the invention.

FIG. 9A shows branches for generating base sequence candidates in the base sequence candidate generator 801, according to an embodiment of the invention. Referring to FIG. 9A, the base sequence candidate generator 801 generates sequence branches ($S_T$) 902 in the prefix and suffix directions when recovery is performed from a position 901 in which a base A exists. Although the branches $S_T$ 902 are generated by considering all cases of all bases A, T, G, and C in FIG. 9A, the base sequence candidate generator 801 generates base sequence candidates by using branches $S_T$ 902 within a range satisfying a predefined threshold. This is described with reference to FIG. 9B.

Figure 9B:
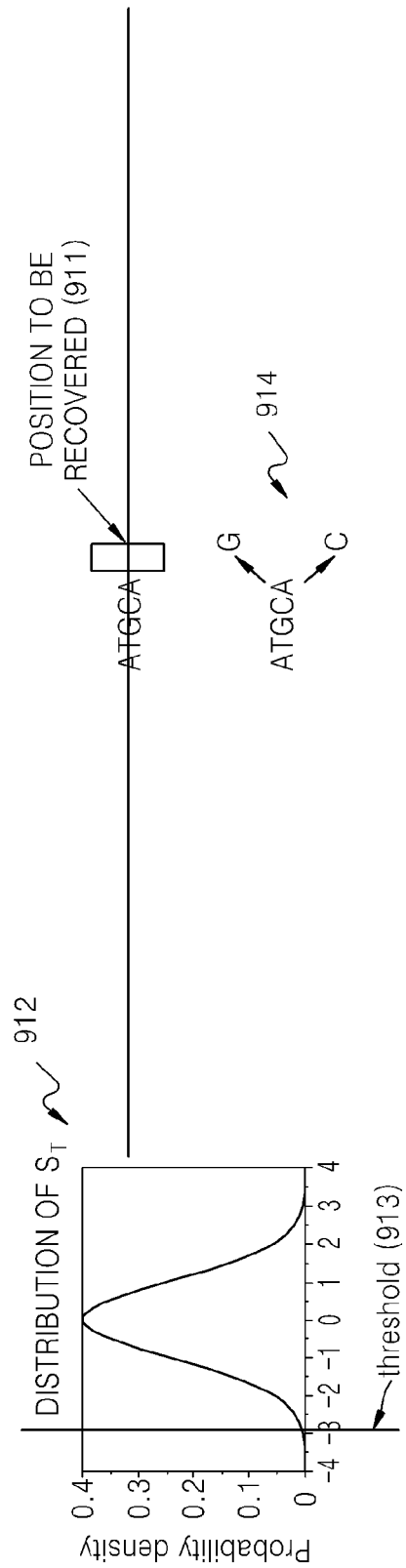
FIG. 9B is a schematic diagram showing generation of base sequence candidates in the base sequence candidate generator, according to an embodiment of the invention.

FIG. 9B shows generation of base sequence candidates in the base sequence candidate generator 801, according to an embodiment of the invention. Referring to FIG. 9B, a distribution 912 of branches $S_T$ from a position 911 to be recovered is shown. The base sequence candidate generator 801 generates base sequence candidates 914 only for branches $S_T$ satisfying a preset threshold 913 from among the branches $S_T$ included in the distribution 912. That is, when bases of the branches $S_T$ satisfying the threshold 913 for the position 911 to be recovered are G and C, the base sequence candidate generator 801 generates ATGCAG and ATGCAC as the base sequence candidates 914.

Figure 9C:
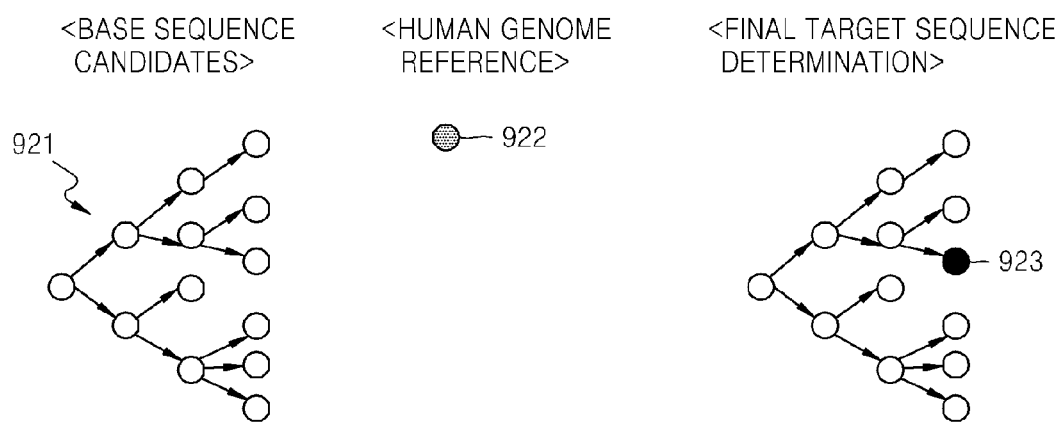
FIG. 9C is a schematic diagram showing determination of a base sequence of a target sequence among base sequence candidates in a base sequence determiner, according to an embodiment of the invention.

FIG. 9C shows determination of the base sequence of a target sequence among base sequence candidates in the base sequence determiner 802, according to an embodiment of the invention. As described in FIG. 9B, the base sequence candidate generator 801 generates base sequence candidates 921.

Referring to FIG. 9C, the base sequence determiner 802 compares the base sequence candidates 921 with a reference sequence 922. The reference sequence 922 can be for example the known base sequence information of the human genome, the known base sequence information for a particular race, or the known base sequence information of one of the relatives of the individual providing the target sequence being recovered. The comparison between the base sequence candidates and reference sequence 922 may be performed by using a known sequence comparison algorithm, e.g., the Basic Local Alignment Search Tool (BLAST), the Blast-Like Alignment Tool (BLAT), FAST-All (FASTA), or the Smith Waterman Algorithm. As a result, the base sequence determiner 802 determines the most similar base sequence candidate among the base sequence candidates 921 as the base sequence of target sequence 923.

Figure 9D:
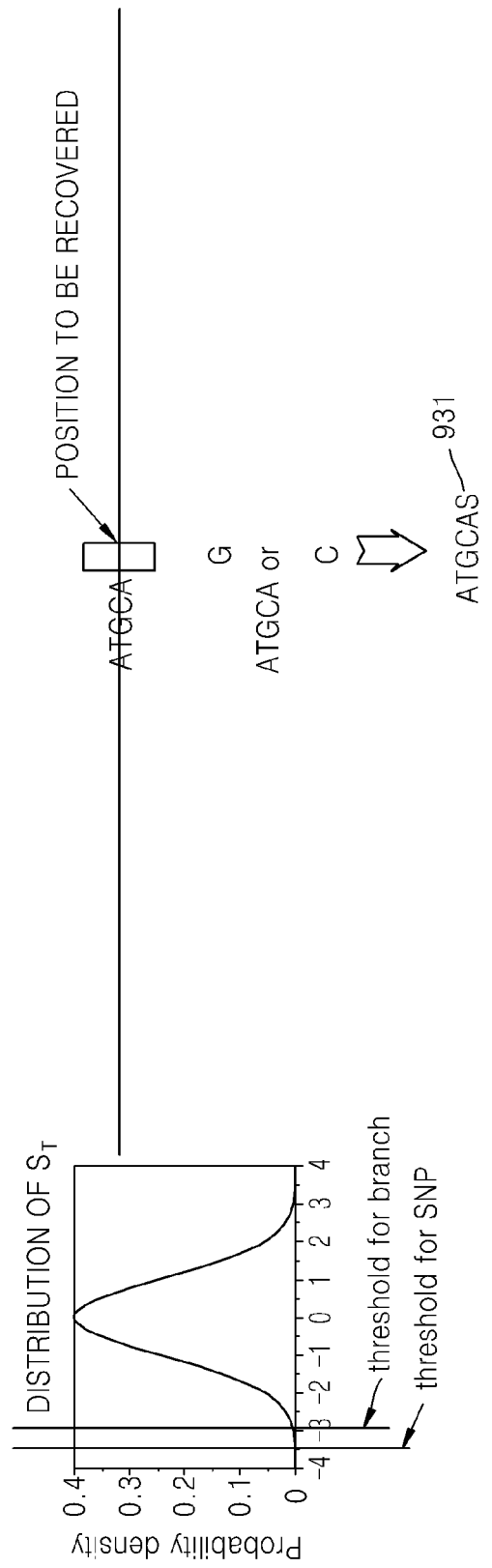
FIG. 9D is a schematic diagram showing determination of a base sequence of a target sequence in the base sequence determiner, according to another embodiment of the invention.

FIG. 9D shows determination of a base sequence of a target sequence in the base sequence determiner 802, according to another embodiment of the invention. Referring to FIG. 9D, the base sequence determiner 802 determines the base sequence of the target sequence by using International Union of Pure and Applied Chemistry (IUPAC) ambiguity codes corresponding to bases included in the candidate sequences. The current embodiment shown in FIG. 9D may be utilized to determine the base sequence of a Single Nucleotide Polymorphism (SNP). In this case, the base sequence candidate generator 801 may preset and use a threshold for only the SNP, which is different from the threshold 913 of FIG. 9B.

In more detail, as described in FIG. 9B, the base sequence candidate generator 801 generates ATGCAG and ATGCAC as base sequence candidates. That is, the base sequence candidates ATGCAG and ATGCAC have different last bases G and C, respectively. In this case, the base sequence determiner 802 according to another embodiment of the invention determines ATGCAS 931 as the base sequence of the target sequence by using the ambiguity code S, which denotes the bases G and C. That is, unlike FIG. 9C, the base sequence determiner 802 according to another embodiment of the invention determines the base sequence of the target sequence by using an ambiguity code instead of determining the target sequence by comparing candidates with a reference sequence.

Figure 10:
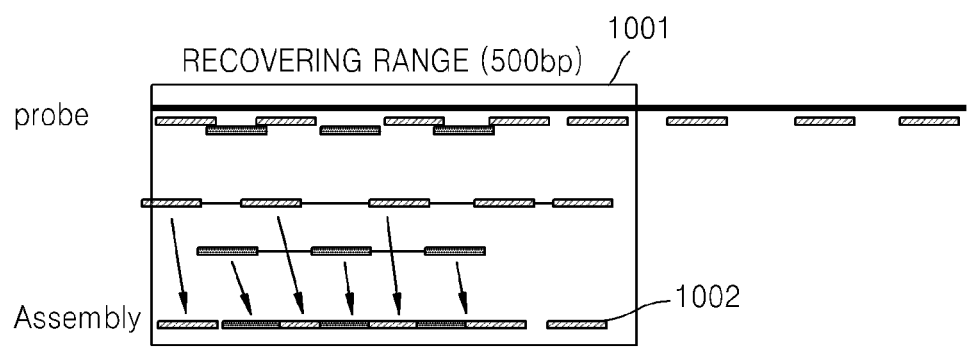
FIG. 10 is a schematic diagram showing recovering within a predetermined recovering range in a recovering unit, according to an embodiment of the invention.

FIG. 10 shows recovering a target sequence within a predetermined recovering range in the recovering unit 30, according to an embodiment of the invention. Referring to FIG. 10, the recovering unit 30 recovers or assembles a target sequence 1002 by using mapping information of different probes included in a probe map within a recovering range 1001 of 500 bp. Thereafter, the recovering unit 30 recovers a final full target sequence by concatenating the target sequence 1002 within the recovering range 1001 and target sequences within the other recovering ranges.

Referring back to FIG. 1A, the recovering unit 30 recovers a target sequence by repeatedly performing the above-described method until the target sequence is completed. The recovered target sequence may be provided to a user through an input/output device (not shown) and/or a display device (not shown) capable of interfacing with the user.

The recovering of the target sequence in the recovering unit 30 may be performed by an algorithm disclosed in Table 2.

TABLE 2

Sequence S recovered to an $(n-1)^{th}$ position
In an $n^{th}$ position, when probe pointer=m and probe length=k (usually k=6), m=n.
When m<n+k, i∈{a, t, g, c}
    partial sequence subseq(S, m−k+1, m−1)+i
        calculate $d_{3'i}$ (an absolute value of a difference between n and an observed position of each partial sequence)
    $s_{3'm} = s_{3'm-1} + d_{3'i}$
    $seq_{3'm} = seq_{3'm-1} + i$
    m=m+1.
When m>n−k, i∈{a, t, g, c}
    partial sequence i+subseq(S, m−k+1, m−1)
        calculate $d_{5'i}$ (an absolute value of a difference between n and an observed position of each partial sequence)
    $s_{5'm} = s_{5'm-1} + d_{5'i}$
    $seq_{5'm} = seq_{5'm-1} + i$
    m=m−1.
$s_T = s_{3'm} + s_{5'm}$
$seq_T = subseq(seq_{5'm}, 0, k-2) + seq_{3'm}$ $m_{apn} = Map(S_T, S_{eql})$
Obtain Set A (Set of $seq_T$) in which $S_T$>threshold in $m_{apn}$.
If size of Set A = 1, charAt($seq_T$, 2k−2) is a base in the $n^{th}$ position.
If size of Set A > 1, generate branches in which charAt($seq_T$, 2k−2) is a base in the $n^{th}$ position for a sequence $seq_T$ of each Set.
Determine a sequence most similar to a reference sequence among all branches as a recovered sequence.

As described above, the nucleic acid sequence recovering apparatus 1 may more correctly recover a target sequence by aligning probes with consideration of errors and determining positions in which the probes are hybridized. In addition, the nucleic acid sequence recovering apparatus 1 may more efficiently and correctly recover a target sequence by recovering the target sequence with respect to all base sequences in both directions and recovering the target sequence with respect to a plural number of cases when the number of cases of a base in a position to be recovered is plural.

Figure 11A:
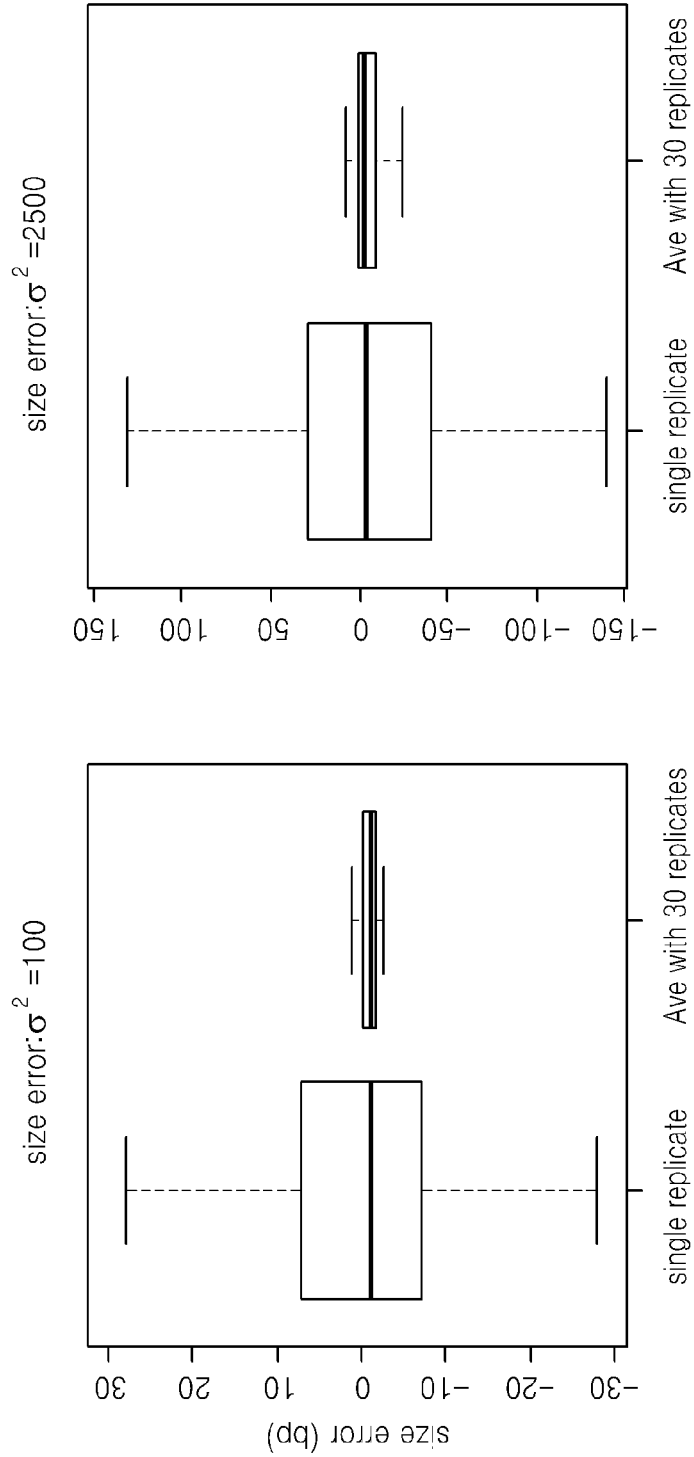
FIG. 11A presents graphs showing the accuracy of target sequences recovered by the recovering unit under different conditions as reduction in position error for a hybridization position, according to an embodiment of the invention.
Figures 11B, 12:
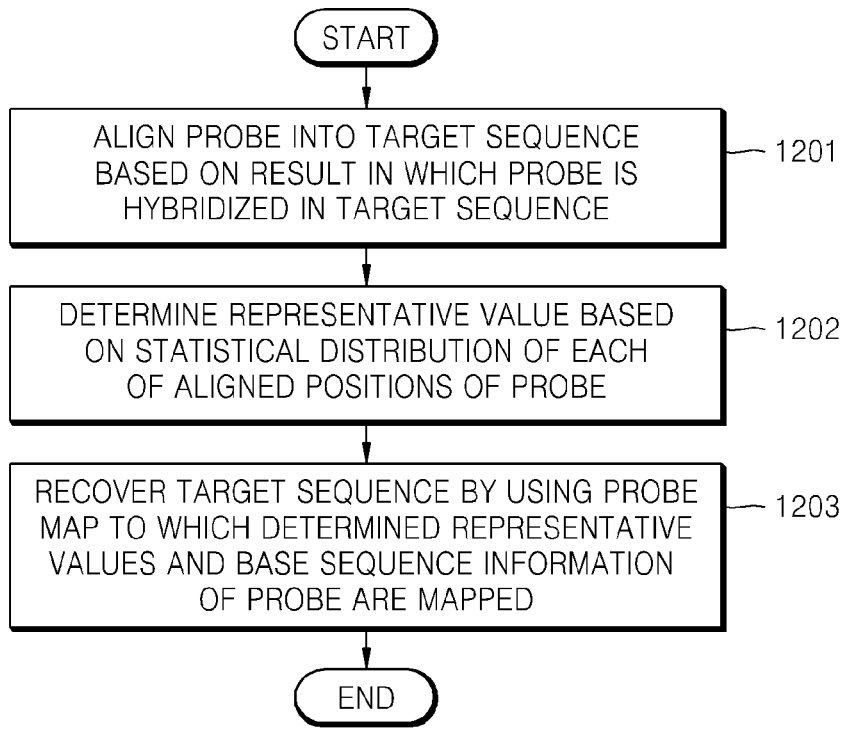
FIG. 11B is a table showing accuracy of target sequences recovered by the recovering unit under different conditions, according to an embodiment of the invention, the column labeled "recovered seq (%)" presents the percent of recovered sequences that correctly match the target.
FIG. 12 is a flowchart of a nucleic acid sequence recovering method according to an embodiment of the invention.

FIGS. 11A and 11B show accuracy of target sequences recovered by the recovering unit 30 under different conditions, according to an embodiment of the invention.

Referring to FIG. 11A, the left graph shows a case of recovering a target sequence based on a once detected hybridization result and a case of recovering a target sequence based on 30 times detected hybridization results. Comparing the two cases with each other, the accuracy of the target sequence shown on the right of the left graph is greater than that of the case on the left thereof, as shown by the greatly reduced error bars reflecting a reduction in position error for the hybridization position. Likewise, the right graph shows the same tendency. Thus, when the probe alignment unit 10 of FIG. 1A aligns probes based on a relatively large number of times detected hybridization results, accuracy of the recovered target sequence may be enhanced.

Comparing the left graph with the right graph, a size error distribution $\sigma^2$ is 100 for the left graph and 2500 for the right graph. Comparing the accuracy of the target sequence in the left graph with that in the right graph, as the size error distribution $\sigma^2$ is small, the accuracy of the target sequence is enhanced.

Referring to FIG. 11B, a table for comparing accuracies of recovered target sequences with each other according to a size error in a position in which a probe is hybridized and the number of detected times is shown. That is, accuracy of a recovered target sequence is enhanced when the standard deviation of the size error is small and/or the number of replicate detected times is increased.

FIG. 12 is a flowchart of a nucleic acid sequence recovering method according to an embodiment of the invention. Referring to FIG. 12, the nucleic acid sequence recovering method according to the current embodiment includes operations sequentially processed by the nucleic acid sequence recovering apparatus 1 shown in FIG. 1A. Thus, although omitted hereinafter, the disclosure associated with the nucleic acid sequence recovering apparatus 1 shown in FIG. 1A is also applied to the nucleic acid sequence recovering method according to the current embodiment.

In operation 1201, the probe alignment unit 10 aligns a probe onto a target sequence based on a result in which the probe having a base sequence of a predetermined length is hybridized to the target sequence.

In operation 1202, the representative value determiner 20 determines a representative value representing each of the aligned positions of the probe based on the statistical distribution of replicate determinations of each of the aligned positions.

In operation 1203, the recovering unit 30 recovers the base sequence of the target sequence by using a probe map to which determined representative values and base sequence information of the probe are mapped.

Figure 13:
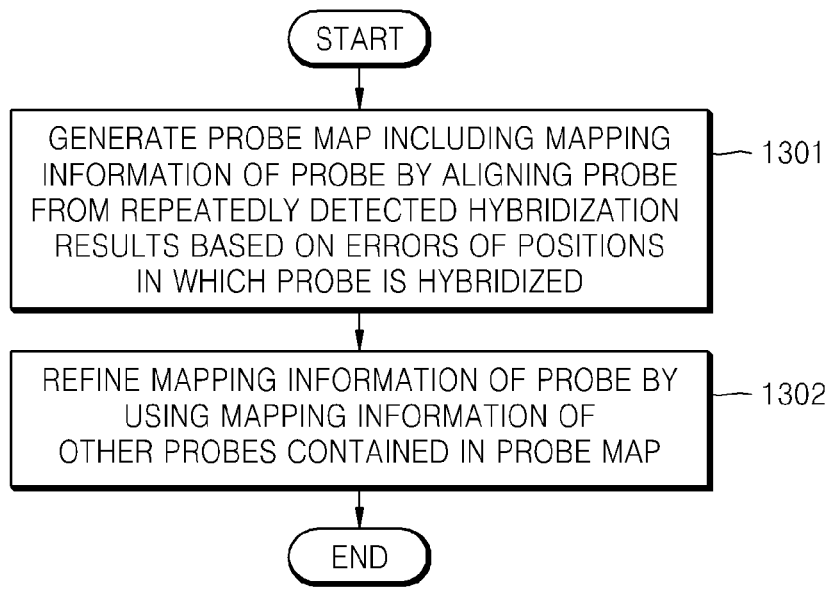
FIG. 13 is a flowchart of an aligning method performed by the probe alignment unit, according to an embodiment of the invention.

FIG. 13 is a flowchart of an aligning method performed by the probe alignment unit 10, according to an embodiment of the invention.

Referring to FIG. 13, in operation 1301, the stretching unit 110 generates a probe map including mapping information of a probe by aligning the probe from repeatedly detected hybridization results considering errors of positions at which the probe is hybridized.

In operation 1302, the polishing unit 120 refines the mapping information of the probe by using mapping information of other probes contained in the probe map.

Figure 14:
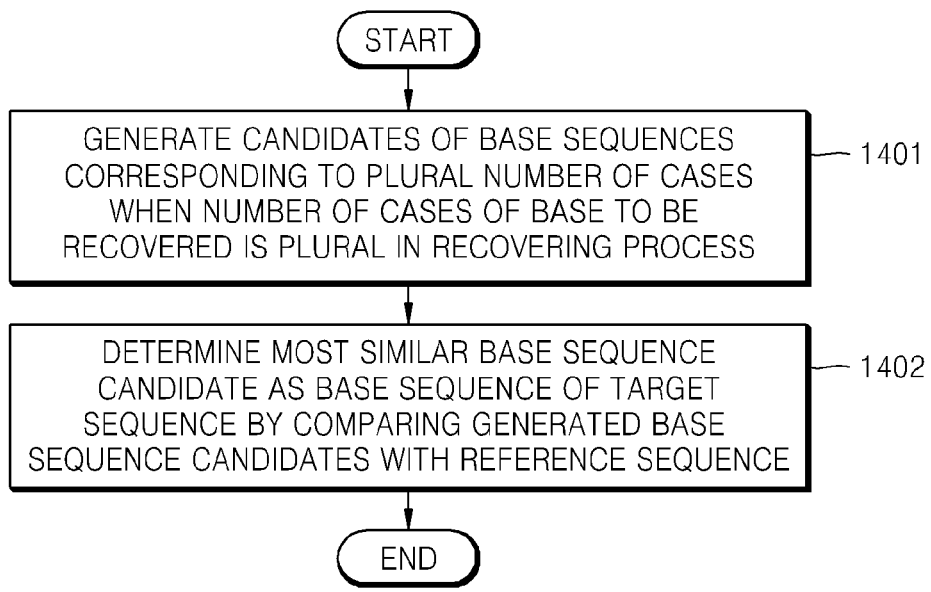
FIG. 14 is a flowchart of a recovering method performed by the recovering unit, according to an embodiment of the invention.

FIG. 14 is a flowchart of a recovering method performed by the recovering unit 30, according to an embodiment of the invention.

Referring to FIG. 14, in operation 1401, the base sequence candidate generator 801 generates candidates of base sequences corresponding to a plural number of cases when the number of cases of a base to be recovered in the recovering process is plural.

In operation 1402, the base sequence determiner 802 determines the most similar base sequence candidate as the base sequence of the target sequence by comparing generated base sequence candidates with a reference sequence.

As described above, according to the one or more of the above embodiments of the invention, a nucleic acid sequence recovering apparatus may recover an error-robust and correct target sequence by aligning probes with the target sequence with consideration of errors and determining positions at which the probes are hybridized. In addition, since the nucleic acid sequence recovering apparatus recovers a target sequence by considering base sequences in opposite directions from the position(s) to be recovered and recovers a target sequence by considering each case when the number of cases of a base in a position to be recovered is plural, the nucleic acid sequence recovering apparatus may recover the target sequence more efficiently and correctly than before.

In addition, other embodiments of the present invention can also be implemented through computer readable code or instructions in or on a medium, e.g., a non-transient computer readable medium, to control at least one processing element to implement any of the above described embodiments. The non-transient medium can correspond to any medium permitting the storage and/or transmission of the computer readable code.

The computer readable code can be recorded/transferred on a non-transient medium in a variety of ways, with examples of the medium including recording media, such as magnetic storage media (e.g., ROM, floppy disks, hard disks, etc.) and optical recording media (e.g., CD-ROMs, or DVDs).

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to"). The modifier "about" used in connection with a quantity is inclusive of the stated value and has the meaning dictated by the context (e.g., includes the degree of error associated with measurement of the particular quantity).

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described herein should be considered in a descriptive sense only and not for purposes of limitation. Descriptions of features or aspects within each embodiment should typically be considered as available for other similar features or aspects in other embodiments.

What is claimed is:

1. A method of recovering a nucleic acid sequence using a probe map, the method comprising:
   aligning a probe having a base sequence of a predetermined length onto a target sequence based on a result in which the probe is hybridized to the target sequence;

determining a representative value representing each aligned position of the probe based on a statistical distribution of each aligned position of the probe; and recovering a base sequence of the target sequence by using a probe map to which the determined representative values and base sequence information of the probe are mapped, wherein the aligning and determining steps are repeated for other probes having base sequences different from the probe, and the probe map contains mapping information of all aligned probes, wherein the aligning, determining, and recovering steps are performed using one or more processors, and wherein the method further comprises generating the probe map containing the mapping information of the probe by aligning the probe from repeatedly detected hybridization results based on errors of positions in which the probe is hybridized; and refining the mapping information of the probe by using the mapping information of the other probes contained in the probe map.

2. The method of claim 1, wherein aligning the probe comprises minimizing an error of a position at which the probe is hybridized to the target sequence.

3. The method of claim 1, wherein refining the mapping information comprises
performing the alignment by referring to mapping information of probes having a base sequence of which at least one base is different from the probe from among the mapping information contained in the probe map.

4. The method of claim 1, wherein determining a representative value comprises
when the statistical distribution is a normal distribution, determining a value representing the normal distribution as the representative value.

5. The method of claim 1, wherein determining a representative value comprises
when the statistical distribution is not a normal distribution, determining the representative value by performing a Monte Carlo simulation with a mathematical model of a Markov chain for the aligned result.

6. The method of claim 1, wherein recovering the base sequence comprises
recovering the base sequence of the target sequence from a position to be recovered by using information regarding positions and base sequences of probes neighboring the position to be recovered in the target sequence, which is contained in the probe map.

7. The method of claim 6, wherein recovering the base sequence comprises
recovering the base sequence of the target sequence by using information regarding positions and base sequences of probes neighboring in both a 5' end direction and a 3' end direction from the position to be recovered.

8. The method of claim 6, wherein recovering the base sequence comprises:
when the number of cases of a base to be recovered in the recovering is plural,
generating base sequence candidates corresponding to the plural number of cases;
comparing the generated base sequence candidates with a reference sequence to determine the base sequence candidate most similar to the reference sequence; and
determining the most similar base sequence candidate is the base sequence of the target sequence.

9. The method of claim 6, wherein recovering the base sequence comprises:
when the number of cases of a base to be recovered in the recovering is plural,
generating base sequence candidates corresponding to the plural number of cases; and
determining the base sequence of the target sequence to be the base sequence represented by the International Union of Pure and Applied Chemistry (IUPAC) ambiguity code corresponding to the bases contained in the base sequence candidates.

10. A non-transient computer-readable recording medium storing a computer-readable program for executing the method of claim 1.

11. An apparatus for recovering a nucleic acid sequence using a probe map, the apparatus comprising:
a probe alignment unit which aligns a probe having a base sequence of a predetermined length onto a target sequence based on a result in which the probe is hybridized to the target sequence;
a representative value determiner which determines a representative value representing each aligned position of the probe based on a statistical distribution of each aligned position of the probe; and
a recovering unit which recovers a base sequence of the target sequence by using a probe map containing mapping information of probes hybridizing to the target sequence, wherein the mapping information for the probe comprises determined representative values and base sequence information of the probe,
wherein the probe alignment unit comprises:
a stretching unit which generates the probe map by aligning a probe from repeatedly detected hybridization results based on errors of positions in which the probe is hybridized; and
a polishing unit which refines the mapping information of a probe by using the mapping information of other probes contained in the probe map;
and wherein the probe alignment unit, stretching unit, polishing unit, representative value determiner, and recovering unit comprise one or more processors.

12. The apparatus of claim 11, wherein the probe alignment unit aligns the probe so that an error of a position in which the probe is hybridized is minimized.

13. The apparatus of claim 1, wherein the polishing unit aligns the probe by referring to mapping information of probes having a base sequence of which at least one base is different from the probe from among the mapping information contained in the probe map.

14. The apparatus of claim 11, wherein, when the statistical distribution is a normal distribution, the representative value determiner determines a value representing the normal distribution as the representative value.

15. The apparatus of claim 11, wherein the recovering unit recovers the base sequence of the target sequence from a position to be recovered by using information regarding positions and base sequences of probes neighboring the position to be recovered in the target sequence contained in the probe map.

16. The apparatus of claim 15, wherein the recovering unit recovers the base sequence of the target sequence by using information regarding positions and base sequences of probes neighboring in both a 5' end direction and a 3' end direction from the position to be recovered.

17. The apparatus of claim 15, wherein the recovering unit comprises:

a base sequence candidate generator which, when the number of cases of a base to be recovered in the recovering is plural, generates base sequence candidates corresponding to the plural number of cases; and a base sequence determiner which determines the base sequence of the target sequence by comparing the generated base sequence candidates with a reference sequence to determine the base sequence candidate most similar to the reference sequence, wherein the base sequence candidate generator and base sequence determiner are provided by one or more processors.

18. The apparatus of claim 15, wherein the recovering unit comprises:

a base sequence candidate generator which, when the number of cases of a base to be recovered in the recovering is plural, generates base sequence candidates corresponding to the plural number of cases; and a base sequence determiner which determines the base sequence of the target sequence using an International Union of Pure and Applied Chemistry (IUPAC) ambiguity code corresponding to bases contained in the base sequence candidates, wherein the base sequence candidate generator and base sequence determiner are provided by one or more processors.

* * * * *